United States Patent [19]

Lichtenstein et al.

[11] Patent Number: 4,492,258
[45] Date of Patent: Jan. 8, 1985

[54] STERILE URINE SPECIMEN COLLECTION

[75] Inventors: Joseph Lichtenstein, Colonia; Vincent Vaillancourt, Livingston, both of N.J.

[73] Assignee: Whitman Medical Corporation, Clark, N.J.

[21] Appl. No.: 467,904

[22] Filed: Feb. 18, 1983

[51] Int. Cl.³ .............................................. B65B 3/04
[52] U.S. Cl. ......................................... 141/1; 141/98; 141/286; 141/331; 4/301; 73/863.41; 128/761; 210/531; 422/102; 604/329
[58] Field of Search ............... 604/329, 327, 347, 349, 604/350; 422/102, 58, 103; 128/761; 210/531; 4/301, 144.1, 144.2, 144.3, 144.4, 450, 451, 462, 114.1; 73/863.41, 863.51, 863.52, 863.61; 141/331-345, 285-310, 198-205, 115-127, 86, 98

[56] References Cited

U.S. PATENT DOCUMENTS

| 3,583,388 | 6/1971 | Hovick | 128/761 |
| 3,635,091 | 1/1972 | Linzer et al. | 128/761 |
| 3,722,503 | 3/1973 | Hovick | 128/761 |
| 3,750,647 | 8/1973 | Gleason et al. | 128/761 |
| 3,830,107 | 8/1974 | Linzer | 128/761 |
| 3,943,770 | 3/1976 | McDonald | 128/761 |
| 3,982,898 | 9/1976 | McDonald | 128/761 |
| 4,040,791 | 8/1977 | Kuntz | 128/761 |
| 4,094,020 | 6/1978 | Franklin | 128/761 |
| 4,252,132 | 2/1981 | Kuntz | 128/761 |
| 4,276,889 | 7/1981 | Kuntz et al. | 128/761 |
| 4,331,162 | 5/1982 | Kuntz et al. | 128/761 |

FOREIGN PATENT DOCUMENTS 1574864  9/1980  United Kingdom ............... 128/761

Primary Examiner—Houston S. Bell, Jr.
Attorney, Agent, or Firm—Holman & Stern

[57] ABSTRACT

Sterile urine specimen collection is achieved by collecting the initial or forestream portion of a void in a chamber and then directing the midstream overflow into a specimen container in which the chamber is partially disposed. Overflow from the specimen container is drained to ambient or to an overflow container. This specimen container is selectively disengageable from the apparatus and can be sealed with a sterile cap which is secured to the apparatus in a sterile manner before it is deployed on the specimen container. Collection of the forestream and terminal portions of the void eliminates dripping from the unit when the specimen container is removed. When the terminal portion is drained to ambient, the drain tube is provided with a drip prevention structure. Void urine is received in a funnel having an oval entrance and a discharge spout which projects into the forestream chamber to a level above overflow holes defined in the chamber. A urine-absorbent material is disposed in the forestream chamber to immobilize the collected forestream and thereby minimize intermixing of the collected forestream with the overflowing midstream.

37 Claims, 9 Drawing Figures

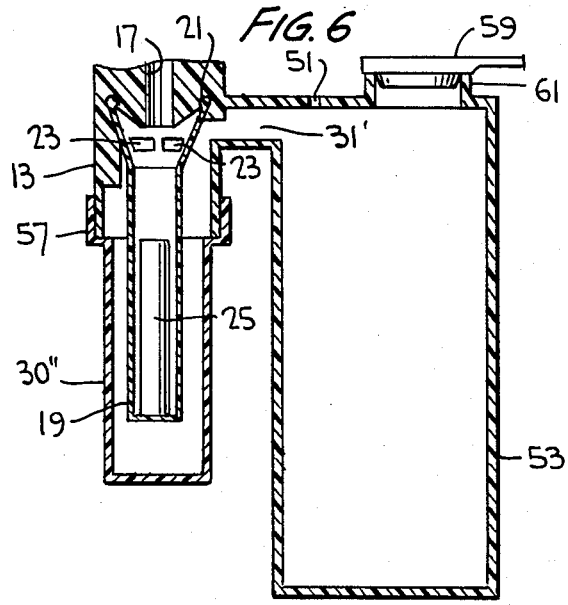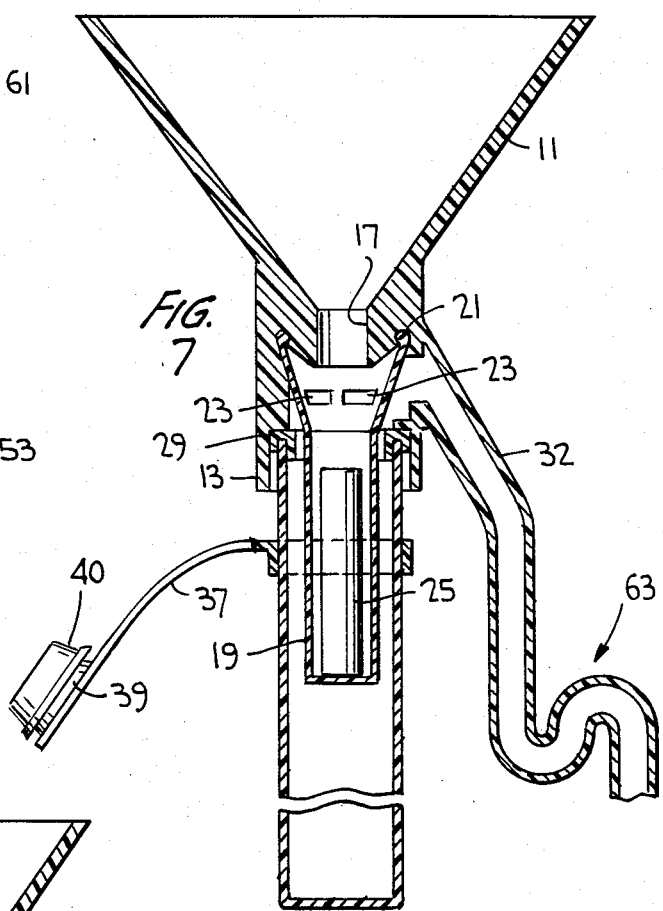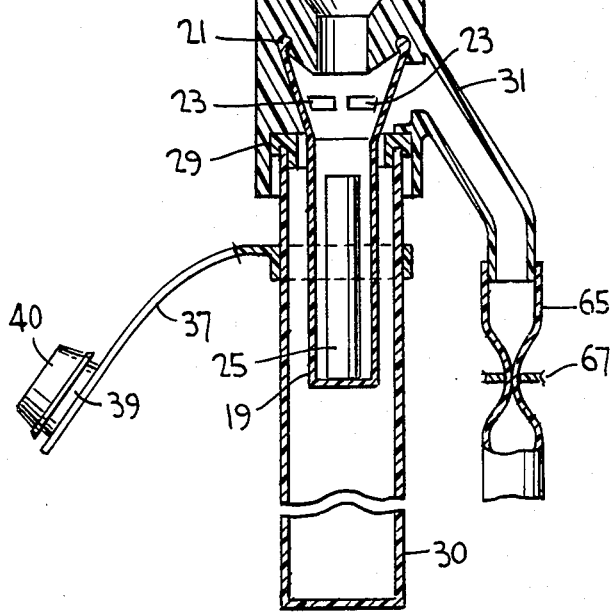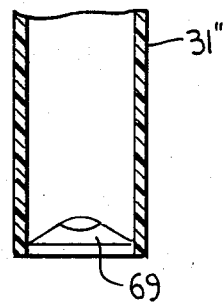

STERILE URINE SPECIMEN COLLECTION

BACKGROUND OF THE INVENTION

1. Technical Field

The present invention relates to a method and apparatus for collecting sterile urine samples for analysis. More particularly, the present invention relates to the sterile collection of the midstream portion of void urine in a simple manner, with inexpensive apparatus, and without spillage or dripping of the forestream and terminal portions of the void.

2. The Prior Art

In collecting urine samples for medical testing and analysis, it is important that the collected sample be as free from contaminants as possible. Contaminants in the urethra and other areas of the urinary tract render straightforward collection of sterile urinary samples somewhat difficult. The problem of contamination is even greater for women patients than for men because of the location of the urethral opening just superior to the vaginal opening. Secretions and other contaminants which collect in the vaginal area, including the labia majora and labia minora, are a particularly troublesome source of urine specimen contamination. It is therefore desirable that the collected sample consist of a midstream portion of a urine void so that the urethra and other areas of the urinary tract, as well as the related portions of the vaginal area, can be flushed out with the initial or forestream portion of the void before the sample for analysis is passed for collection. However, midstream urine collection is not an easy procedure, primarily because it is difficult for a patient to interrupt a void stream so as to pass only part of the stream before collecting sample. As a consequence, numerous devices have been proposed in the prior art for automatically collecting midstream portions of a urine void. Examples of these devices may be found in U.S. Pat. Nos. 3,583,388 (Hovick), 3,635,091 (Linzer et al.), 3,722,503 (Hovick), 3,750,647 (Gleason et al.), 3,830,107 (Linzer et al.), 3,943,770 (McDonald), 3,982,898 (McDonald), 4,040,791 (Kuntz), 4,094,020 (Franklin), 4,276,889 (Kuntz et al.) and 4,331,162 (Kuntz et al.). In spite of these devices, problems still exist in the art of midstream urine collection. For example, certain of these prior art midstream collection devices require relatively complex structure which form-fits a woman's vaginal area. Such devices, apart from their complexity and expense, are psychologically rejected by many women patients who simply prefer not to use them. Others of these patented devices require expensive and/or bulky structure to select the midstream portion of a void. Still others have inherent leakage problems wherein the initial void portion and/or the terminal void portion tends to leak or drip after the midstream sample container has been disconnected or disassociated from the rest of the apparatus. For example, the devices disclosed in the aforementioned U.S. Pat. Nos. 4,276,889 and 4,331,162 (Kuntz et al.) direct the forestream or initial void portion into a chamber having a bleed hole in its bottom. Experience has shown that urine tends to drip from this bleed hole after the specimen container has been removed and during disposal of the chamber. This dripping is not favored by medical personnel who have to handle the device.

The aforesaid Kuntz et al patents rely on a build-up of urine level in the initial void bleed chamber before the urine overflows into a surrounding toroidal specimen container. It is possible, particularly in the case of patients with urinary tract disorders, that the bleed rate from the chamber bleed hole will exceed or equal the patient's void rate; or, the patient's void rate may exceed the bleed rate by too small a difference for the level in the chamber to reach the overflow opening. Under such circumstances, the device cannot collect the desired midstream sample.

Many of the prior art midstream collection devices rely on directing the forestream portion of the void into a chamber and then diverting or overflowing the midstream portion into a specimen container when the urine level in the chamber reaches some predetermined level. In such devices, unless the assembly is held absolutely still the forestream portion is jostled and tends to intermix to some degree with the diverted or overflowing midstream portion. This intermixing results in contamination of the midstream portion by contaminants in the forestream portion.

Another problem of prior art midstream urine collection units relates to the difficulty with which the midstream specimen container is disassociated from the rest of the unit and transported to the analysis location. In many prior art units the entire unit and not just the specimen container must be transported. In units where the specimen container can be relatively easily disassociated from the rest of the unit, the disassociated specimen container is not readily sealed without contaminating the collected specimen.

OBJECTS IN SUMMARY OF THE INVENTION

It is therefore an object of the present invention to provide a method and apparatus for collecting a midstream specimen of void urine wherein the specimen is easily disassociated from the remainder of the unit and sealed in a sterile manner and wherein the remainder of the unit can be disposed of without leakage or dripping.

It is another object of the present invention to provide a method and apparatus for collecting a midstream specimen of void urine which eliminates or minimizes contamination of the specimen by the initial or forestream portion of the void when the unit is inadvertently moved or jostled during and after voiding.

Another object of the present invention is to provide a method and apparatus for collecting a midstream specimen of void urine wherein the specimen is collected in a simple and sterile manner irrespective of a patient's void rates.

In accordance with the present invention, midstream urine specimen collection is achieved by directing the initial or forestream portion of the void stream into a forestream collection chamber which contains a urineabsorbent solid body. The absorbent solid body, pellets, flakes or powder, immobilizes the collected forestream portion, thereby preventing it from intermixing with the subsequently received midstream portion which overflows the forestream collection chamber from overflow openings located below the chamber inlet. The lower portion of the forestream collection chamber projects through the open top of a midstream specimen collection container so that overflow from the chamber flows down along the chamber side and into the specimen container. When the specimen container is full, it overflows into a drain passage which is directed into a drain chamber or, alternatively, downward to ambient for flow into a toilet facility. A sterile cap is secured to the unit in a sterile manner and is deployable over the top of the specimen container when the container is removed from the unit. The specimen container is engaged to the unit by friction fit, threaded engagement or other easily disruptable engagement. Collection of the forestream portion of a void in a separate chamber precludes any leakage of the forestream portion during voiding or after the specimen is disengaged. The terminal or drain portion of the void is prevented from leaking by collecting it in a drain container or by contouring the vented drain passage to prevent dripping.

The presence of the lower portion of the forestream collection chamber in the specimen container during midstream collection assures that the volume of urine collected in the specimen container is less than the container capacity. Therefore, when the specimen container is disengaged from the unit, the forestream collection chamber is withdrawn from the specimen container and the liquid level in the container recedes below overflowing. As a consequence, no spillage or leakage occurs upon disengagement of the specimen container.

BRIEF DESCRIPTION OF THE DRAWINGS

These and other objects, features and many of the attendant advantages of the invention will be better understood upon a reading of the following detailed description when considered in connection with the accompanying drawings wherein like parts in each of the several figures are identified by the same reference numbers, and wherein:

FIG. 6 is a broken view in vertical section of still another embodiment of the present invvention;

FIG. 7 is a view in vertical section of still a further embodiment of the present invention;

FIG. 8 is a view in vertical section of another embodiment of the present invention;

FIG. 9 is a view in section of an alternative drain tube configuration for the various embodiments described and illustrated herein.

DESCRIPTION OF THE PREFERRED EMBODIMENTS

Figure 1:
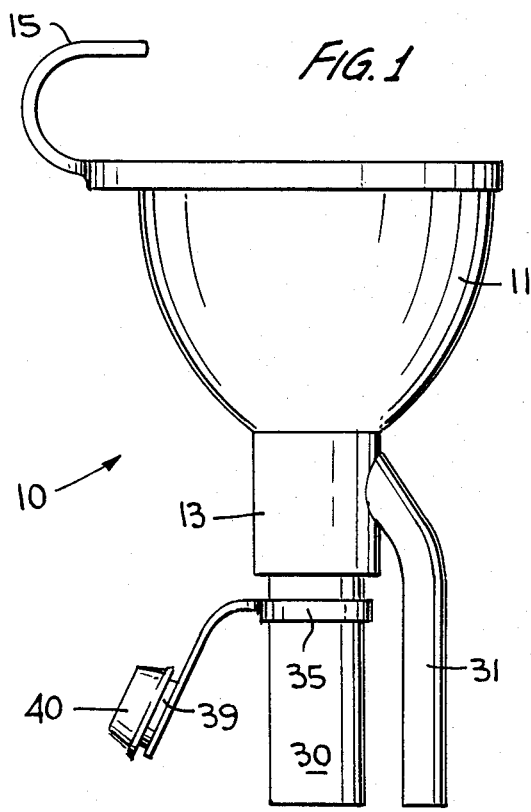
FIG. 1 is a side view in elevation of one embodiment of a midstream specimen collection apparatus of the present invention.
Figure 2:
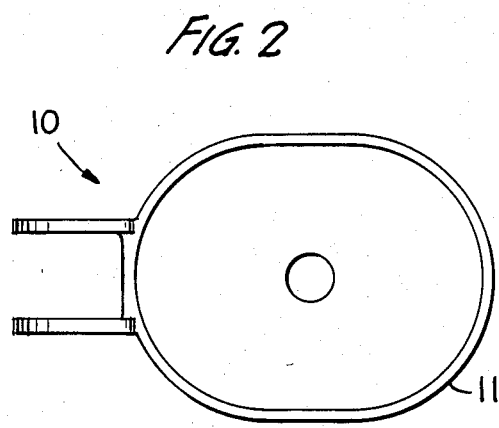
FIG. 2 is a top view of the embodiment of FIG. 1.
Figure 3:
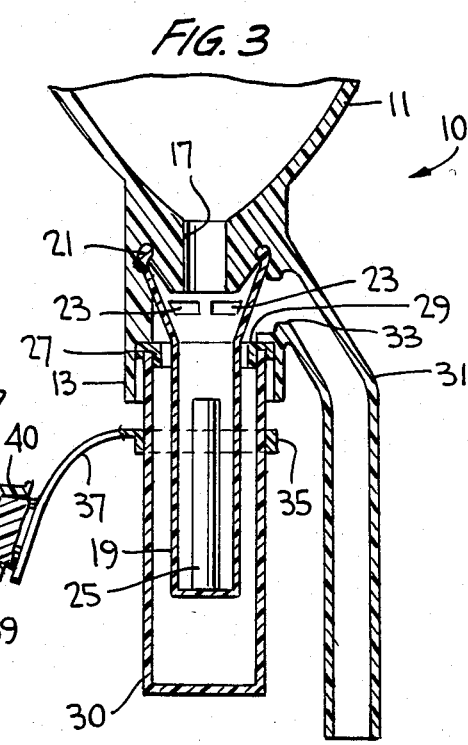
FIG. 3 is a broken view in vertical section of the embodiment of FIG. 1.

Referring specifically to FIGS. 1, 2 and 3 of the accompanying drawings, a midstream specimen collection assembly is generally designated by the reference numeral 10. A urine stream collecting or receiving funnel 11 has a generally oval opening at its top and a depending annular sleeve 13 at its bottom. A handle 15 is secured to, and is preferably integrally formed with, the funnel 11 at the lip of the top opening. Handle 15 is disposed along the major axis of the oval opening (i.e. at a side having a smaller radius of curvature) so that the opposite side may be easily positioned between the patient's legs to receive a urine void stream. Handle 15 has a generally C-shaped configuration with its open side facing radially inward. With this handle configuration a patient can readily hold the unit with his or her index finger inside the open C-shaped configuration and his or her thumb on the top leg of the handle; alternatively, the handle may be grasped with the thumb inside the handle opening and two or three fingers on the outer handle surface. The oval funnel configuration, apart from facilitating deployment of the unit in use, minimizes bulk and maximizes the target area for the void stream, particularly for female patients.

Interiorly of sleeve 13 and above its lower end there is a funnel discharge outlet 17 which is preferably disposed at the radial center of the funnel to discharge all liquid received through the open upper end of the funnel. A collection chamber 19 for the initial or forestream portion of void urine is disposed directly below discharge outlet 17 to receive all liquid discharged through that outlet. In the illustrated embodiment, discharge outlet 17 takes the form of an annular projection extending downwardly within outer sleeve 13. The juncture between the outer surface of outlet 17 and the inner surface of the sleeve 13 is contoured to receive an annular lip 21 of chamber 19 in a snap-fit engagement. The upper portion of chamber 19 includes a downwardly tapered section which is bounded at its top by lip 21. The bottom portion of chamber 19, which is axially longer than the tapered portion, is generally cylindrical and projects concentrically down through sleeve 13. A plurality of angularly spaced overflow outlet openings 23 are defined in chamber 19 in its tapered upper portion. Lip 21 is secured about the discharge outlet 17 such that the bottom of the discharge outlet terminates at a level which is axially between lip 21 and openings 23 in chamber 19. The opening of discharge outlet 17 has a smaller diameter than the diameter of the tapered portion of chamber 19 at overflow openings 23 so that liquid discharged through outlet 17 cannot flow directly into outlets 23 unless chamber 19 is filled. A solid body member 25, which may also be porous foam or the like made of urine-absorbent material, is disposed within chamber 19 which, except for its open inlet end at lip 21 and overflow outlet openings 23, is entirely closed. Member 25 may be made of super absorbent cellulose as one example of a copolymer or other material which will absorb urine in the chamber 19.

An annular downwardly-facing shoulder 27 is defined on the inner wall of annular sleeve 13. An annular rubber seal 29, having an inverted generally U-shaped vertical cross-section, has its base and one leg secured to shoulder 27 and the inner wall of sleeve 13, respectively. The open end of the seal 29 receives the annular upper edge of an open-top midstream specimen collection container 30 having a generally cylindrical configuration. Container 30 is open at its top but is otherwise enclosed. When received in seal 29, container 30 is positioned in radially-spaced concentric relation about lower portion of forestream collection chamber 19 which projects a considerable axial distance into the container. The friction-fit engagement of the container 30 in seal 29 permits the container to be disconnected or disassociated from the funnel and chamber 19 by merely pulling downward on the container while slightly rotating it about its longitudinal axis.

With midstream specimen collection container 30 connection in seal 29, overflow outlet openings 23 in chamber 19 are positioned above the top of container 30 and above the annular space subsisting between the radially inner portion of seal 29 and the exterior of chamber 19. This annular space serves as an annular ingress opening for liquid which overflows chamber 19 via openings 23.

A drain passage 31 has its upper or inlet end extending generally downward and away from the annular space above seal 29 and adjacent overflow outlet 23 of chamber 19. A radially inner side of drain passage 31 forms a weir-like structure 33 over which flows the overflow liquid from midstream specimen collection container 30. Drain passage 31 takes the form of a tube, the lower portion of which extends downward, parallel to container 30, on the side of the assembly 10 which is diametrically opposed to that on which the handle 15 is located.

A plastic or rubber retainer ring 35 is secured about container 30 in a friction-fit or permanent engagement, if desired. A flexible strap 37 extends radially from retainer ring 35 and has a cap 39 secured to its upwardly facing side. A cover 40 hermetically seals cap 39 which takes the form of a plug that can be inserted into the upper end of container 30 to seal the container when the latter is removed from seal 29.

As illustrated, funnel 11, sleeve 13 and drain tube 31 are integrally formed as a common unit in the preferred embodiment. Forestream collection chamber 19 and midstream specimen collection container unit 30 are separately formed, although only container 30 is intended to be separated from assembly 10 as part of the assembly utilization procedure. In use, the collection assembly 10 is grasped by handle 15 so that the upper end of funnel 11 is positioned to receive a void urine stream. The initial or forestream portion of the void is discharged past overflow outlet 23 into forestream collection chamber 19 where it is absorbed and immobilized by absorbent body 23. After the initial volume of the void liquid fills chamber 19 up to the level of overflow outlets 23, liquid subsequently discharged from outlet 17 overflows through outlets 23, through the annular space between chamber 19 and seal 29, into midstream specimen collection container 30. After container 30 has been filled, further overflow through openings 23 flows over weir-like structure 33 and down through drain tube 31. It is presumed that the collection procedure is performed over a toilet or other waste receptacle so that the terminal portion of the void which is drained via drain tube 31 can be disposed of properly.

It is to be noted that the volume of urine collected in midstream collection container 30 is less than the capacity of this container by an amount equal to the outer volume of the lower portion of chamber 19 which extends into container 30. The outer volume of this lower portion of chamber 19 is greater than the volume of the annular space which exists between the very top of container 30 and the tip of weir-like structure 33. This permits the void liquid which resides in this annular space to fall into container 30 when the container is pulled away from the assembly and chamber 19 is withdrawn from within the container. If the liquid in the annular space above container 19 could not be accomodated within the volume previously occupied by the chamber 19, this liquid would spill or leak out of the assembly when the container is disconnected from the seal. Therefore, the positioning of chamber 19 within the container 30 serves not only to render the assembly compact and easy to handle, but also to eliminate spillage and leakage upon removal of the specimen container.

Absorbent body 25 prevents the forestream liquid in chamber 19 and its contaminants from mixing with the subsequently received midstream portion of a void. Without body member 25 in chamber 19 the initial forestream liquid might tend to recirculate and mix with the newly discharged liquid from egress outlet 17. Moreover, such mixture would almost certainly take place, without body member 25, as the assembly 10 is moved about during and immediately after the void procedure.

When voiding is terminated, the specimen container 30 is easily removed from seal 29 and then capped by plug 39 after removal of cover 40 from the plug. The remainder of the assembly may then be thrown away. Alternatively, the remainder of the assembly may be cleaned and sterilized and then re-used with another container 30; however, disposability is a desirable and preferred feature of the present invention.

Figure 4:
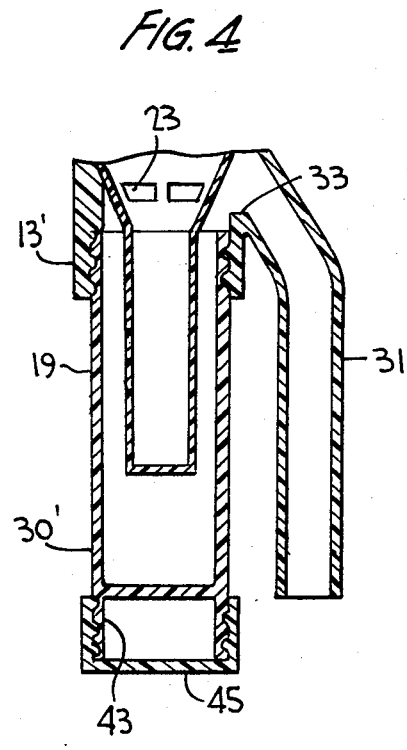
FIG. 4 is a broken view in vertical section of an alternative embodiment of the present invention.

Referring specifically to FIG. 4 of the accompanying drawings, a portion of a modified embodiment of the invention is illustrated. This embodiment differs from that of FIGS. 1–3 in two respects. First, instead of seal 29 and a friction-fit engagement of the specimen container, the interior wall of bottom sleeve 13' is threaded to receive the threaded outer wall of the upper end of specimen container 30'. Second, the bottom of container 30' is provided with an annular extension which is threaded on its outer wall to engage the threaded interior wall of a cap 45. The threaded interior wall of cap 45 is arranged to engage the threads at the top of container 30'. Thus, container 30' is selectively removable from the assembly by unscrewing it from sleeve 13'. The disengaged container can then be capped by cap 45 which is first disengaged from annular extension 43.

Figure 5:
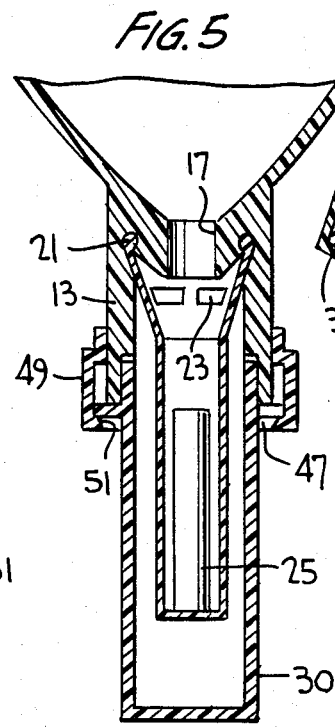
FIG. 5 is a broken view in vertical section of a further embodiment of the present invention.

Another arrangement for permitting selective disengagement of the specimen container from the assembly is illustrated in FIG. 5, to which reference is now made. Container 30 is provided with a radially-extending annular ledge 47 on its outer wall at a location below its upper end.

An annular, flexible pinch clamp member 49 is secured to the outer wall of sleeve 13 and has an annular lip 51 which engages the underside of ledge 47 from above. Container 30 is supported in the assembly in this manner until it is desired to disengage the container. Disengagement is effected by exerting radially inward forces at two or more locations on clamp 49 above ledge 47. This causes the clamp to pivot on the outer edge of ledge 47 to force lip 51 radially outward until it clears or substantially clears ledge 47. The interior surface of lip 51 may be sloped, as shown, to facilitate removal of container 30 without requiring lip 51 to be fully retracted by the radially-inward force supplied to the clamp.

The midstream collection assembly of the present invention may be adapted for use at locations where toilet facilities are not readily available. An embodiment adapted for such use is illustrated in FIG. 6 to which specific reference is now made. In this embodiment the drain passage 31' extends only a short distance from its inlet and terminates in an inlet opening to a terminal void portion container 53. This container has a relatively large volume so as to accommodate the terminal portion to be expected in most urine void procedures. A vent opening 55 is defined in a top wall of terminal portion container 53 to permit air to escape and be replaced by the terminal overflow through drain path 31'.

The embodiment of FIG. 6 also includes an alternative means for removably attaching the specimen container 30″ to the assembly. In this embodiment, the specimen container has an upper section 57 which has a larger diameter than the rest of the container. The inner wall of the container section 57 is proportioned to engage the outer wall of sleeve 13 in a friction fit. A cap 59 for sealing the upper section 57 of container 30″ is provided with a depending plug portion which fits inside the upper container section. When the cap is not in use, its plug portion is engaged with a friction fit in an annular cap retainer disposed atop terminal portion container 53.

As noted above, by collecting the initial or forestream portion of the void rather than bleeding or draining it, a considerable leakage and dripping problem is eliminated. It is also desirable to avoid dripping from the drain tube 31 after the void procedure has terminated. An embodiment for achieving this is illustrated in FIG. 7 wherein the drain tube 32 is provided with a goose neck trap 63 proximate its outlet end. The trap 63 collects any residual liquid in the bottom bend and thereby avoids dripping. Alternatively, the drain tube 31 of FIG. 3 may be internally coated with silicone or other non-wetting material to eliminate retention or cling of liquid to the inner wall of the tube and thereby eliminate dripping.

The embodiment of FIG. 8 has a foreshortened drain tube 31 with a flexible hose 65 secured to its discharge end as an extension. A clamp 67 is selectively applied to the hose to pinch it closed and prevent dripping. Alternatively, hose 67 may be bent upward to avoid postvoid dripping from the assembly.

In FIG. 9 the drain tube 31″ is illustrated with an internal frusto-conical plug or baffle 69 at its lower end. Baffle 69 projects back into the drain tube and has a central raised opening for passing flow. Residual liquid is collected below the raised opening to prevent dripping.

From the foregoing description it will be appreciated that the invention makes available a novel method and apparatus for simply and inexpensively collecting midstream portions of void urine without leakage and contamination. The forestream collection chamber 19 typically collects a volume of 10 cc of the initial void liquid. The volume of the specimen container 30 is somewhat larger and depends upon the volume of urine required for testing and analysis. The method and apparatus described herein permit a simple operation with no need for maneuvering the funnel for midstream catch of the desired sample. The initial contaminated void is diverted and immobilized to prevent it from intermixing with the portions of the void subsequently received. The specimen container can be readily removed in a simple manner without being accidentally contaminated. Moreover, the patient is able to cap the specimen container aseptically.

Having described several embodiments of a new and improved method and apparatus for sterile urine specimen collection according to the present invention, it is believed that other modifications, variations and changes will be suggested to those of ordinary skill in the art in light of the disclosure herein. It is therefore to be understood that all such variations, modifications and changes are believed to fall within the scope of the invention as defined by the appended claims.

What is claimed is:

1. Apparatus for collecting a midstream portion of void urine, said apparatus comprising:
   a midstream specimen collection container having an inlet opening;
   a forestream collection chamber having an upper end with an inflow opening defined therein, a closed lower end and overflow outlet means disposed between said inflow opening and said closed lower end for overflowing all liquid entering said forestream collection chamber after the liquid level therein reaches a first predetermined level;
   means for selectively securing said midstream specimen collection container relative to said forestream collection chamber with the closed lower end of said forestream collection chamber extending into said midstream collection container through said inlet opening and with said overflow outlet means disposed outside said midstream specimen collection container;
   liquid receiving means for receiving a void urine stream and discharging the received urine through said inflow opening in said forestream collection chamber;
   wherein said inlet opening of said midstream specimen collection container is sufficiently wider than the periphery of the lower end of the forestream collection chamber extending therethrough to provide an inlet flow path into said midstream specimen collection container for liquid which overflows from said forestream collection chamber through said overflow outlet means; and
   drain means for receiving subsequent overflow of liquid from said inlet opening of said midstream specimen collection container.

2. The apparatus according to claim 1 wherein said liquid receiving means is a funnel having a generally oval and relatively wide inlet and a small discharge opening projecting into said forestream collection chamber through said inflow opening to a level above said overflow outlet means.

3. The apparatus according to claim 2 wherein said overflow outlet means comprises at least one overflow opening defined through said forestream collection chamber at said first predetermined level in said chamber.

4. The apparatus according to claim 3 wherein said upper end of said forestream collection chamber has a generally funnel shaped configuration in which said inlet opening is relatively wide, said generally funnel shaped configuration having a tapered portion which converges downwardly and wherein said at least one overflow opening is defined in said tapered portion.

5. The apparatus according to claim 4 wherein said drain means is a flow passage which conducts said subsequent overflow of liquid downwardly and externally of said apparatus.

6. The apparatus according to claim 4 wherein said drain means comprises a reservoir for collecting said subsequent overflow of liquid.

7. The apparatus according to claim 4 further comprising urine immobilizing means disposed within said forestream collection chamber, said urine immobilizing means comprising a urine-absorbent material.

8. The apparatus according to claim 4 further comprising:
   a cap which is deployable to engage said midstream specimen collection container to seal said inlet opening when the midstream specimen collection container is removed relative to said forestream collection chamber;

means for removably attaching said cap in a medically sterile manner to said apparatus for subsequent removal and deployment to engage said midstream specimen collection container.

9. The apparatus according to claim 4 wherein said drain means comprises:

a drain path extending generally downward to ambient from a location adjacent said forestream collection chamber and above said inlet opening of said midstream specimen collection container; and drip prevention means for preventing residual dripping of urine from said path after flow of said subsequent overflow through said drain path has terminated.

10. The apparatus according to claim 2 further comprising a handle secured to said funnel, said handle being secured proximate the top of said funnel and having a generally C-shaped configuration with an open side facing generally horizontally and generally inward toward said funnel.

11. The apparatus according to claim 10 wherein said drip prevention means comprises a goose neck liquid trap bend in said drain tube.

12. The apparatus according to claim 10 wherein said drain tube has an outlet end and wherein said drip prevention means comprises a small volume liquid collection region within said drain tube disposed proximate the outlet end of said drain tube.

13. The apparatus according to claim 10 wherein said drip prevention means comprises a non-wetting coating on the interior wall of said drain tube.

14. The apparatus according to claim 1 wherein said outlet overflow means comprises a plurality of angularly spaced overflow openings defined through said forestream collection chamber at said first predetermined level.

15. The apparatus according to claim 1 further comprising urine immobilizing means disposed within said forestream collection chamber, said urine immobilizing means comprising a urine-absorbent material.

16. The apparatus according to claim 1 further comprising:

a cap which is deployable to engage said midstream specimen collection container to seal said inlet opening when the midstream specimen collection container is removed relative to said forestream collection chamber;

means for removably attaching said cap in a medically sterile manner to said apparatus for subsequent removal and deployment to engage said midstream specimen collection container.

17. The apparatus according to claim 1 wherein said drain means comprises:

a drain path extending generally downward to ambient from a location adjacent said forestream collection chamber and above said inlet opening of said midstream specimen collection container; and drip prevention means for preventing residual dripping of urine from said path after flow of said subsequent overflow through said drain path has terminated.

18. The apparatus according to claim 1 wherein said liquid receiving means and said drain means are part of an integrally-formed member having a downwardly open sleeve depending therefrom, said apparatus further comprising means for securing said forestream collection chamber interiorly of said integrally-formed member such that the lower end of the chamber projects outwardly through said sleeve.

19. The apparatus according to claim 18 wherein said means for selectively securing said midstream specimen collection container comprises a threaded engagement between said sleeve and said container.

20. The apparatus according to claim 18 wherein said means for selectively securing said midstream specimen collection container comprises a releasable two-part clamp unit having first and second mutually-engageable and selectively-releaseable members secured to said sleeve and said container, respectively.

21. The apparatus according to claim 18 wherein said means for selectively securing said midstream specimen collection container comprises a press-fit concentric engagement between said sleeve and said container.

22. Apparatus for collecting a midstream portion of void urine, said apparatus comprising:

a urine stream receiving member having a relatively wide inlet opening for receiving void urine, a relatively small discharge opening for discharging received urine and a contour which directs all urine received at said inlet opening to said discharge opening;

a forestream collection chamber having an upper end which has an opening to receive urine discharged from said discharge opening of said receiving member, said collection chamber having an overflow outlet means disposed at a predetermined height in said chamber for overflowing all urine received in said chamber after the urine level therein reaches said predetermined height, said chamber, except for said upper end opening and said overflow outlet means, being otherwise fully enclosed;

a selectively detachable midstream specimen collection container having an inlet opening arranged to receive initial overflow of urine through said overflow outlet means;

drain means arranged to receive subsequent overflow of urine through said overflow outlet means after the level of urine in said specimen collection container reaches a predetermined level; and connection means for selectively detaching the specimen collection container from said apparatus.

23. The apparatus according to claim 22 further comprising urine immobilizing means disposed within said forestream collection chamber.

24. The apparatus according to claim 22 wherein said urine immobilizing means comprises a urineabsorbent material.

25. The apparatus according to claim 22 wherein said drain means comprises a drain tube arranged to conduct urine received by it to the environment external to said apparatus.

26. The apparatus according to claim 25 further comprising drip prevention means for preventing dripping of urine from said drain tube after urine flow through the drain tube has terminated.

27. The apparatus according to claim 26 wherein said drip prevention means comprises a goose neck liquid trap bend in said drain tube.

28. The apparatus according to claim 26 wherein said drain tube has an inlet end wherein said drip prevention means comprises a small volume liquid collection region within said drain tube disposed proximate the outlet end of said drain tube.

29. The apparatus according to claim 26 wherein said drip prevention means comprises a non-wetting coating on the interior wall of said drain tube.

30. The apparatus according to claim 22 wherein said opening in said upper end of said forestream collection chamber has a predetermined size, wherein said discharge opening of said receiving member is smaller than the predetermined size and is at least partially inserted in said opening, and wherein said overflow outlet means comprises at least one overflow opening in said forestream collection chamber, which overflow opening is spaced from said discharge opening at least in the transverse dimension relative to the discharged urine so as not to be in the path of urine discharge from said receiving member into said forestream collection chamber.

31. The apparatus according to claim 22 wherein said upper end of said forestream collection chamber has a generally funnel-shaped configuration in which said opening is relatively wide and wherein said upper end has a tapered portion which tapers radially inward and down, wherein said discharge opening of said receiving means extends downward into said tapered portion in radially spaced relation to said tapered portion, and wherein said overflow outlet means comprises at least one overflowing opening defined through said tapered portion in radially-spaced relation to said discharge opening.

32. The apparatus according to claim 31 wherein said specimen collection container, when attached relative to said forestream collection chamber, is disposed concentrically about said forestream collection chamber and has an open upper end which is radially spaced from said forestream collection chamber at a location below said at least one overflow opening to define an annular inlet space which receives said initial overflow.

33. The apparatus according to claim 32 wherein said drain means comprises a flow passage extending generally radially outward from said annular inlet space and then down to drain said subsequent overflow from said annular inlet space.

34. The apparatus according to claim 22 wherein said drain means comprises an overflow container for collecting said subsequent overflow.

35. The apparatus according to claim 22 wherein said forestream collection chamber includes a bottom portion which extends into said midstream specimen collection container through said inlet opening.

36. A method for collecting a midstream specimen of void urine comprising the steps of:
collecting a forestream portion of void urine in a chamber disposed partially in a midstream collection container;
retaining the collected forestream portion in said chamber while overflowing a subsequent midstream portion of the void urine into said container; and
draining urine which overflows said container.

37. Apparatus for collecting a midstream portion of void urine, said apparatus comprising:
a midstream specimen collection container having an inlet opening;
a forestream collection chamber having an ingress opening;
liquid receiving means for receiving a void urine stream and discharging the received urine into said forestream collection chamber;
overflow means for directing discharged urine from said liquid receiving means into said midstream specimen collection container via said inlet opening when the liquid in said forestream collection chamber is at a predetermined level; and
absorbent means disposed in said forestream collection chamber for absorbing urine received therein.

* * * * *